US010391261B1

(12) United States Patent
Glammeier

(10) Patent No.: US 10,391,261 B1
(45) Date of Patent: Aug. 27, 2019

(54) SYRINGE SECURING SYSTEM

(71) Applicant: Lance Glammeier, Sioux Falls, SD (US)

(72) Inventor: Lance Glammeier, Sioux Falls, SD (US)

(*) Notice: Subject to any disclaimer, the term of this patent is extended or adjusted under 35 U.S.C. 154(b) by 400 days.

(21) Appl. No.: 15/072,047

(22) Filed: Mar. 16, 2016

(51) Int. Cl.
*A61M 5/32* (2006.01)

(52) U.S. Cl.
CPC ........ *A61M 5/3202* (2013.01); *A61M 5/3204* (2013.01); *A61M 5/3213* (2013.01); *A61M 5/3219* (2013.01); *A61M 2005/3215* (2013.01); *A61M 2005/3217* (2013.01)

(58) Field of Classification Search
CPC .... A61M 5/46; A61M 5/3219; A61M 5/3202; A61M 2005/3215; A61M 5/321; A61M 5/50; A61M 2005/3217; A61M 5/3213–3219; A61M 5/3243–3275
See application file for complete search history.

(56) References Cited

U.S. PATENT DOCUMENTS

| | | | |
|---|---|---|---|
| 5,259,840 A * | 11/1993 | Boris | A61M 5/3213 604/110 |
| 6,287,282 B1 * | 9/2001 | Bonaldo | A61M 5/3271 128/919 |
| 2007/0260192 A1 * | 11/2007 | Lee | A61M 5/3243 604/197 |
| 2016/0287797 A1 * | 10/2016 | Olson | A61M 5/3202 |

FOREIGN PATENT DOCUMENTS

| | | | | |
|---|---|---|---|---|
| EP | 0510626 A1 * | 10/1992 | | A61M 5/3213 |
| EP | 0510626 A1 * | 10/1992 | | A61M 5/3213 |

OTHER PUBLICATIONS

Machine Translation of EP 0510626 A1. Acquired on Apr. 25, 2018.*

* cited by examiner

*Primary Examiner* — Jenna Zhang
(74) *Attorney, Agent, or Firm* — Jeffrey A. Proehl; Woods, Fuller, Shultz & Smith, PC

(57) ABSTRACT

A syringe retaining apparatus may include a syringe having a barrel with a main portion and a transition portion, and a needle extending from the transition portion of the barrel. The apparatus may include a protective cap removably mounted on the syringe and configured to receive the needle of the syringe and at least a portion of the transition portion of the barrel of the syringe. The protective cap may have an open proximal end and a closed distal end, and an interior surface and an exterior surface. The apparatus may have a locking structure configured to permit removal of the protective cap from the syringe when the syringe is inserted to a first depth insertion into the cap and resist removal of the protective cap from the syringe when the syringe is inserted into the protective cap to a second depth of insertion.

16 Claims, 4 Drawing Sheets

US 10,391,261 B1

SYRINGE SECURING SYSTEM

BACKGROUND

Field

The present disclosure relates to syringe handling apparatus and more particularly pertains to a new syringe securing system for facilitating safer uncapping and recapping of a syringe during use.

SUMMARY

In one aspect, the present disclosure relates to a syringe retaining system comprising a syringe retaining apparatus which may include a syringe having a barrel with main portion and a transition portion and a needle extending from the transition portion of the barrel. The apparatus may also include a protective cap removably mounted on the syringe and configured to receive the needle of the syringe and at least a portion of the transition portion of the barrel of the syringe. The protective cap may have an open proximal end and a closed distal end, and a tip portion at the distal end. The cap may also have an interior surface and an exterior surface. The apparatus may also include a locking structure configured to permit removal of the protective cap from the syringe when the syringe is inserted to a first depth insertion into the cap and resist removal of the protective cap from the syringe when the syringe is inserted into the protective cap to a second depth of insertion.

In another aspect, the disclosure relates to a syringe retaining system which may include a medicine vial holder comprising a tubular element with an interior passage defined by an inner surface, and a rod on which at least a portion of the tubular element is mounted such that an end portion of the tubular element is substantially hollow. The system may also include a syringe having a barrel with main portion and a transition portion and a needle extending from the transition portion of the barrel. The apparatus may also include a protective cap removably mounted on the syringe and configured to receive the needle of the syringe and at least a portion of the transition portion of the barrel of the syringe. The protective cap may have an open proximal end and a closed distal end, and a tip portion at the distal end. The cap may also have an interior surface and an exterior surface. The apparatus may also include a locking structure configured to permit removal of the protective cap from the syringe when the syringe is inserted to a first depth insertion into the cap and resist removal of the protective cap from the syringe when the syringe is inserted into the protective cap to a second depth of insertion. The protective cap may have at least one exterior ridge on the exterior surface of the protective cap configured to engage the inner surface when the tip portion of the cap is inserted into the interior passage of the tubular element.

In still another aspect, the disclosure relates to a method of using a syringe which may include providing a syringe, a protective cap, and a spacer element configured to limit insertion of the syringe into the protective cap to a first depth of insertion. The method may also include providing a medicine vial holder including a tubular element, inserting a tip portion of the protective cap into the interior passage of the tubular element in a manner such that at least one exterior ridge on the tip portion of the cap engages the inner surface of the tubular element, withdrawing the syringe from the protective cap, and permitting removal of the spacer element from the syringe. The method may also include utilizing the syringe and inserting the syringe into the protective cap to a second depth of insertion such that a first component of a locking structure located on the syringe engages a second component of the locking structure located on the protective cap.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

Figure 1A:
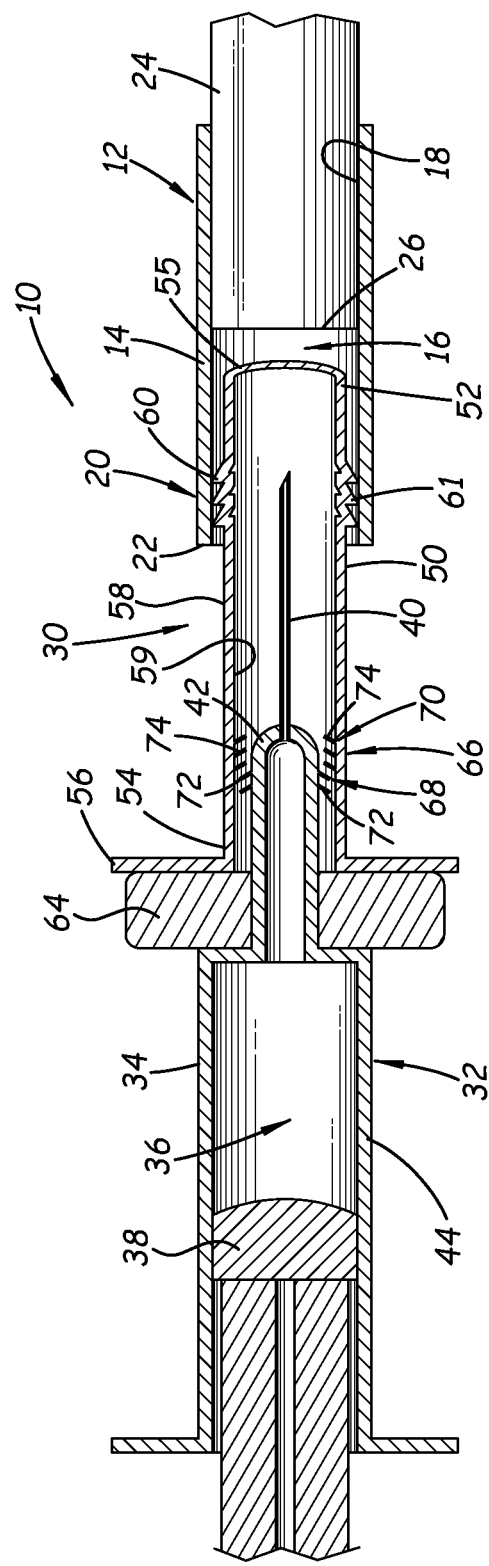
FIG. 1A is a schematic side sectional view of a new syringe securing apparatus and system showing the syringe at a first depth of insertion into the protective cap, according to the present disclosure.
Figure 1B:
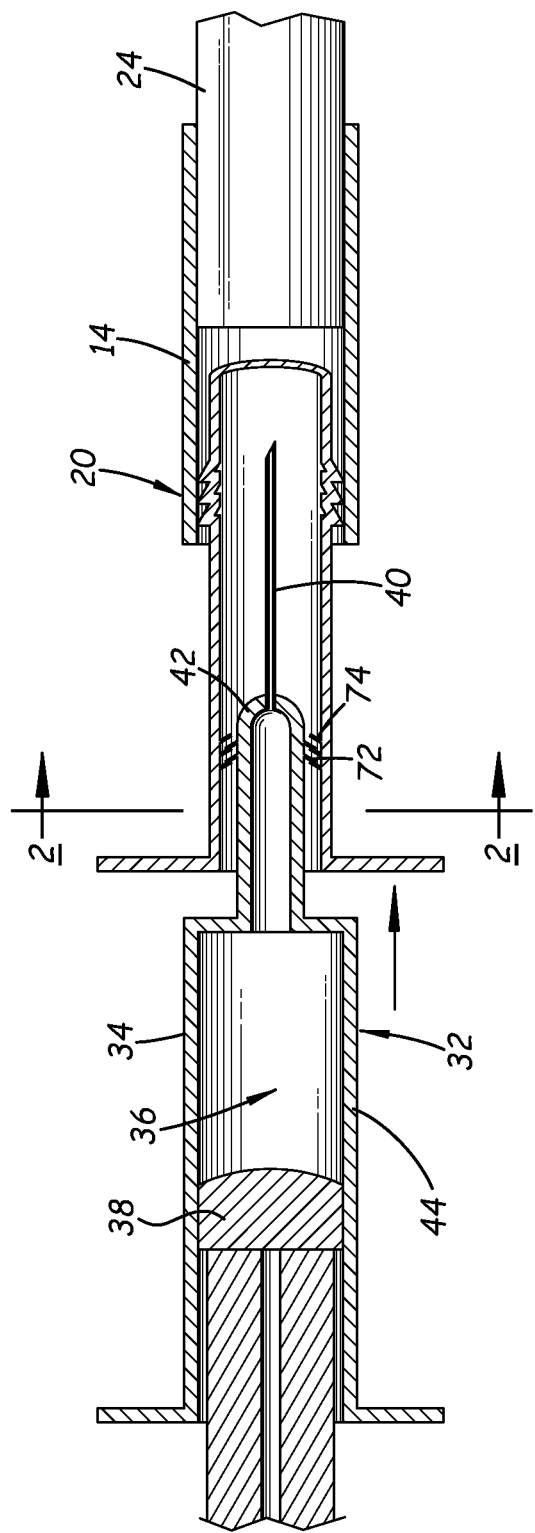
FIG. 1B is a schematic side sectional view of the syringe securing apparatus showing the syringe at a second depth of insertion into the protective cap, according to the present disclosure.
Figure 2:
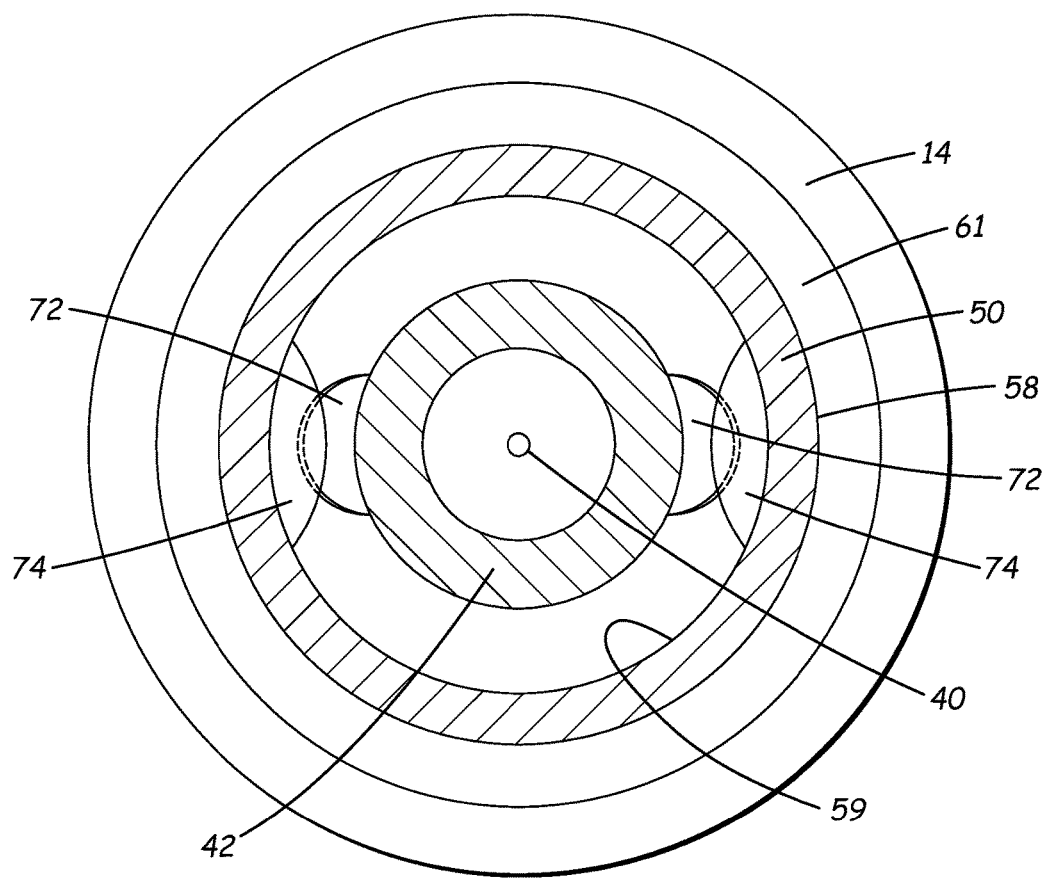
FIG. 2 is a schematic sectional view of the syringe securing apparatus, according to an illustrative embodiment.
Figure 3:
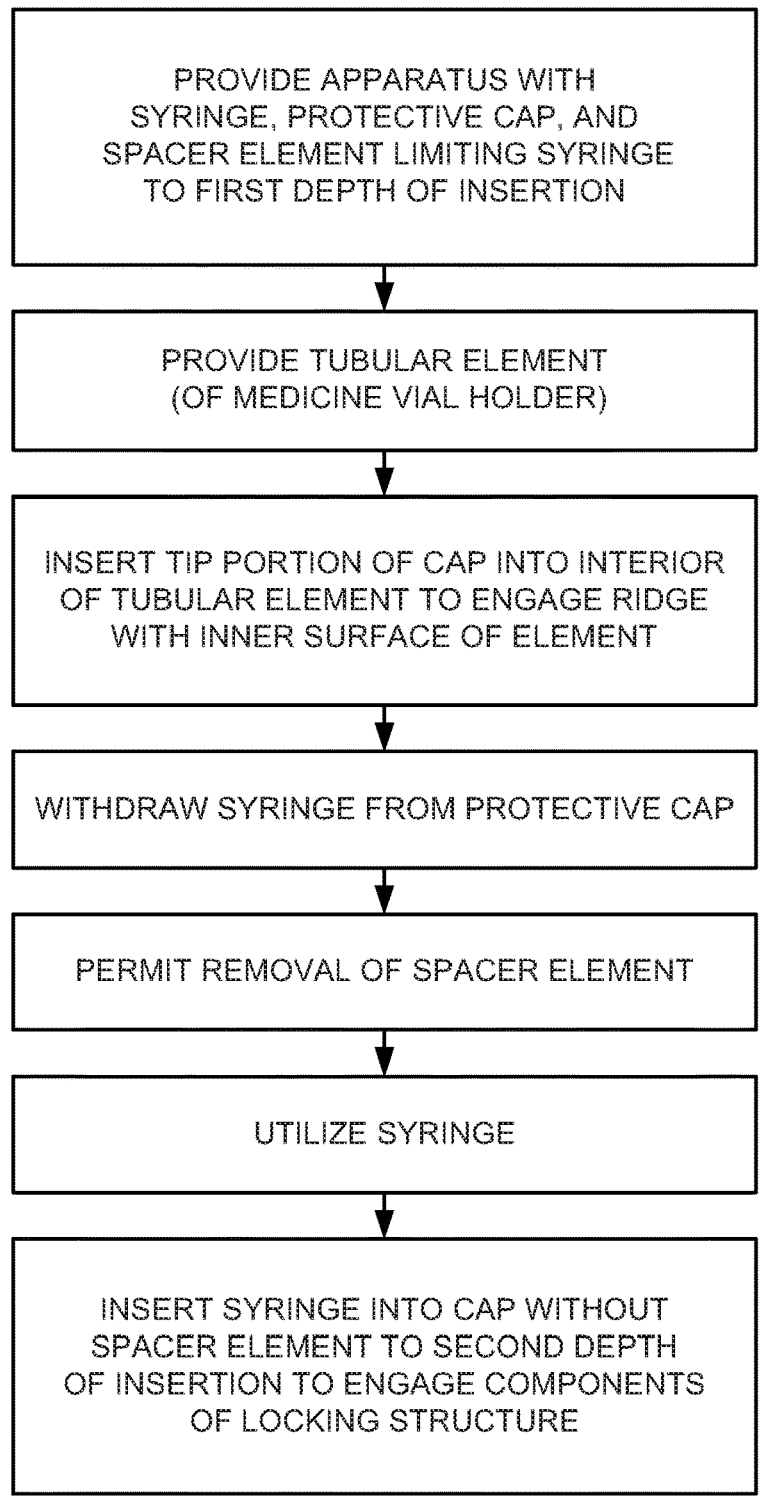
FIG. 3 is a schematic flow diagram of a method for using the system, according to an illustrative implementation.

With reference now to the drawings, and in particular to FIGS. 1 through 3 thereof, a new syringe securing system embodying the principles and concepts of the disclosed subject matter will be described.

The applicant has recognized that the problem of unintended needle sticks or pokes is an ongoing concern for those working in the healthcare industry. However, the administration of drugs through injection remains very common and every injection represents a number of opportunities for the healthcare worker to be unintentionally poked with a syringe needle, including when the protective cap over the needle is removed from the syringe (and the hand of the worker gripping the protective cap is exposed as the cap is removed from the needle), when the protective cap is replaced on the needle of the syringe (and the hand of the worker gripping the cap is again in close proximity to the needle as the needle is inserted into the cap), as well as during the actual act of performing an injection on the patient. Moreover, between removal and replacement of the protective cap, it may be misplaced or unintentionally dropped making it difficult or even impossible to replace the cap on the needle. The applicant has also recognized that once the injection has been performed, the syringe will be disposed of and thus the cap, once replaced on the syringe, will never need to be removed from the syringe again and thus a substantially permanent coupling of the cap on the syringe would be beneficial to maintain the safety provided by the cap until the healthcare worker is able to place the syringe in a disposal container.

To those ends, the applicant has devised a system that provides a convenient dismounting and remounting of the protective cap on a syringe while also providing secure retainage of the cap in a convenient manner while the syringe is being utilized to perform an injection, and then providing a manner of replacement of the cap on the syringe that does not require the user to grip the cap or place his or her hands near the cap or the exposed needle as the cap is being replaced on the syringe. Moreover, in combination with the applicant's patented medicine vial holder and system, the healthcare worker may also avoid the need to hold a medicine vial while withdrawing medicine from the vial into the syringe which can help provide an environment in which potential exposure of the hands and arms of the healthcare worker to the needle of the syringe is minimized not only during the loading of the medicine into the syringe but also during the times that the protective cap of the syringe is removed from and replaced on the syringe.

In some aspects, the disclosure relates to a syringe retaining system 10 which is highly suitable for providing safer removal of a protective cap from a syringe prior to use without the user having to manually remove the cap, which brings the hand of the user in close proximity to the needle once the cap is removed. Further, the system is highly suitable for providing a place to retain the cap while the syringe is being used to reduce if not eliminate the chance for misplacement of the cap during the time that it is not being used. Also, the system is advantageous for providing a means of more safely replacing the cap on the syringe after usage without having to manually handle the cap as the cap is being replaced on the syringe.

In exemplary embodiments, the system 10 may include a medicine vial holder 12 which may be utilized to hold a medicine vial in a secure manner to allow withdrawal of fluid medicine from the interior of the vial into a syringe. Illustrative vial holders are disclosed, for example, in my U.S. Pat. Nos. 8,967,572 and 9,254,241, the disclosures of each being hereby incorporated by reference in their entireties. In part, suitable holder structures may include a tubular element 14 with an interior passage 16 with an inner surface 18 which may have a substantially circular cross-section in some embodiments. The tubular element 14 may also have an end portion 20 and a free end 22 which terminates the end portion. Suitable tubular elements 14 may be formed at least partially of an elastomeric material which may permit resilient stretching of the perimeter wall of the tubular element to permit enlargement of the interior passage when stretching or distending force is applied. The medicine vial holder 12 may also include a rod 24 on which at least a portion of the tubular element 14 is mounted. The tubular element 14 may extend about the rod portion, and the tubular element 14 may extend beyond an end 26 of the rod such that the end portion 20 of the tubular element is substantially hollow and not occupied by the rod 24.

The syringe retaining system 10 may also include a syringe retaining apparatus 30 which is configured to releasably hold the syringe on the vial holder 12 and may also function to lock or otherwise secure a protective cap on the syringe after use of the syringe. The syringe retaining apparatus 30 may include a syringe 32 which includes a barrel 34 which defines an interior 36 for receiving a fluid, a plunger 38 which is movable in the interior of the barrel to exert pressure on fluid in the interior, and a needle 40 which may extend from the barrel 34 and be in fluid communication with the interior of the barrel. The barrel 34 may include a transition portion 42 on which the needle is mounted and may also include a main portion 44 in which the plunger 38 is located and provides the bulk of the storage for the fluid.

The syringe retaining apparatus 30 may also include a protective cap 50 which may be removably mounted on the syringe 32. The cap 50 may be configured to receive the needle 40 of the syringe and at least a portion of the transition portion 42 of the barrel 34 of the syringe. The protective cap 50 may have a proximal end 54 and a distal end 55 at which a tip portion may be generally located. The proximal end 54 may be an open for receiving a portion of the syringe therethrough, and the distal end may be a closed end. The protective cap 50 may have a flange 56 which is positioned at the proximal end of the cap and may extend radially outward from the opening in the end. The protective cap 50 may have an exterior surface 58 which may be substantially cylindrical in shape, and may also have an interior surface 59 which may also be substantially cylindrical in shape.

The cap 50 may have at least one exterior ridge 60 which is configured to engage the tubular element when the tip portion 52 of the cap is inserted into the interior passage 16 of the tubular element to help retain the cap on the tubular element until a sufficient degree of force is applied to the cap to withdraw the cap from the interior passage. The exterior ridge 60 may be configured to engage the inner surface 18 of the tubular element, and the ridge may be configured such that contact and engagement between the ridge 60 and the tubular element causes a degree of distention of the tubular element. The exterior ridge may extend radially outwardly from the exterior surface of the cap, and may extend for a portion of the circumference of the tubular element. The ridge may be located toward the closed end 55 of the cap such that the cap does not need to be fully inserted into the tubular element, but only partially. In some embodiments, at least a pair of exterior ridges 60, 61 may be provided on the exterior surface 58 of the cap and may extend in substantially opposite directions from each other for engaging opposite sections of the inner surface 18 of the tubular element, which may provide a suitable degree of distention of the elastomeric material of the tubular element which in turn provides a degree of resistance to removal of the protective cap from the interior passage 16 of the tubular element 14. In some embodiments, the ridge or ridges may be continuous about the circumference of the cap, while in other embodiments the ridge may be discontinuous about the circumference and may comprise, for example, a plurality of arcuate barbs.

The syringe retaining apparatus 30 may also include a spacer element 64 which is configured to limit the degree of insertion of the syringe into the protective cap when present. When mounted on the syringe 32 and/or the protective cap 50 the spacer element 64, may permit the syringe to only reach a first depth of insertion (see, for example, FIG. 1A) when the spacer element is positioned between the syringe and the cap, and the syringe may be capable of a second depth of insertion (see, for example, FIG. 1B) into the cap when the spacer element 64 is not mounted on or otherwise positioned between the syringe and the cap. The first depth of insertion may represent a partial insertion of the syringe into the cap such that the needle and a portion of the transition portion of the barrel are inserted into the cap, and the second depth of insertion may represent a greater degree of insertion of the syringe into the cap such that the needle and a larger portion of the transition portion is inserted into the cap. The spacer element 64 may extend about the transition portion 42 of the syringe and may be positioned between the main portion 44 of the barrel and the flange 56 of the cap when in place. The spacer element may comprise a loop, although this is not critical. The spacer element 64 may be loosely mounted on the syringe such that removal of the syringe from the protective cap allows the spacer element to be removed or simply fall away from a mounted condition on the syringe.

The syringe retaining apparatus 30 may also include a locking structure 66 which is configured to selectively lock the protective cap 50 on the syringe when the syringe is inserted into the protective cap to the second depth of insertion. The locking structure 66 may comprise a first component 68 on the syringe and a second component 70 on the protective cap. The first 68 and second 70 components may be interlockable with each other when the syringe is inserted into the protective cap to the second depth of insertion, and the interlocked first and second components may be configured to resist removal of the protective cap from the syringe. The first component 68 may comprise at least one first locking tab 72 located on the barrel 34 of the syringe, and which may be located on the transition portion 42 of the barrel. The first locking tab 72 may be inclined away from the needle, and may be inclined toward the main portion 44 of the barrel. In some embodiments, a pair of first locking tabs 72 may be positioned on the syringe and may extend in substantially opposite directions from each other on the syringe. Optionally, additional similarly-configured first locking tabs may be utilized. In some embodiments, the first locking tab or tabs may comprise a first locking barb.

The second component 70 may comprise at least one second locking tab 74 positioned on the protective cap. The second locking tab may be mounted on the interior surface 59 of the cap. The second locking tab 74 may be inclined toward the distal end 55 of the protective cap and away from the proximal end 54 of the cap as the tab 74 extends from the interior surface 59 towards the center of the interior of the cap. In some embodiments, a pair of the second locking tabs 74 may be employed and extend substantially toward each other from opposite sides or locations on the interior surface of the protective cap in a generally opposed relationship. In some embodiments, the second locking tab may comprise a second locking barb.

In some embodiments, the first depth of insertion of the syringe into the protective cap may not result in contact or the interlock of the tabs 72, 74 with each other (see, for example, FIG. 1A), while the second depth of insertion results in the contact and engagement or interlock of at least some of the tabs 72, 74 with each other (see, e.g., FIG. 1B) such that the inserted portion of the syringe is prevented from being withdrawn from the cap. Optionally, a further depth of insertion of the syringe into the cap may be possible such that the tab or tabs 72 pass by the tab or tabs 74 and may even move out of engagement therebetween, but the tabs 72, 74 still prevent or strongly resist the removal of the cap from the syringe. It will be recognized that other configurations of tabs or structures on the syringe and the cap may be utilized to provide the "one-way" passage of the components 68, 70 with respect to each other.

In other aspects, the disclosure relates to a method of using a system 10 in the administration of a medicine using a syringe having one or more of the various features disclosed herein and a syringe retaining apparatus also having one or more of the various features described in this disclosure. The protective cap 50 may be provided on the syringe with a syringe limited by the spacer element 64 to the first depth of insertion. The method may also include providing a medicine vial holder including the tubular element 14. The method may further include inserting a tip portion 52 of the protective cap into the interior passage 16 of the tubular element, and may include engaging the exterior ridge or ridges 60 on the tip portion of the protective cap with the inner surface 18 of the tubular element such that some degree of distention of the elastomeric material of the tubular element is caused by the ridges and results in a degree of resistance to removal of the protective cap from the tubular element. The method may also include withdrawing the syringe from the protective cap, while the cap is held in the interior passage of the tubular element. The method may also include permitting the spacer element 64 on the syringe to be removed from or fall away from the syringe upon withdrawal of the syringe from the protective cap. The method may also include utilizing the syringe, such as to inject or administer a medicinal fluid to a patient. After utilization of the syringe (e.g., to perform an injection), the method may include inserting the syringe into the protective cap to the second depth of insertion such that the first component 68 of the locking structure engages the second component 70 of the locking structure and the interlocking of the first and second components resists, if not completely blocks, removal of the syringe from the protective cap. The syringe and the protective cap thus behave as a unit, and pulling on the syringe causes pulling on the cap and assists in removal of the cap from the tubular element.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps disclosed in the text and/or the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A syringe retaining system comprising:
    a syringe retaining apparatus comprising: a syringe having a barrel with a main portion and a transition portion with a shoulder therebetween, and a needle extending from the transition portion of the barrel;
    a protective cap removably mounted on the syringe, the protective cap being configured to receive the needle of the syringe and at least a portion of the transition portion of the barrel of the syringe, the protective cap having an open proximal end and a closed distal end, the protective cap having a tip portion at the distal end and a flange adjacent to the proximal end, the protective cap having an interior surface and an exterior surface;
    a locking structure configured to permit removal of the protective cap from the syringe when the syringe is inserted to a first depth of insertion into the protective cap and to resist removal of the protective cap from the syringe when the syringe is inserted into the protective cap to a second depth of insertion, the second depth of insertion of the syringe into the protective cap being deeper into the protective cap than the first depth of insertion;
    a spacer element removably mounted in a mounted condition on the transition portion of the syringe in a position between the shoulder of the syringe and the flange of the protective cap, the mounted condition of the spacer element being characterized by permitting the syringe to be inserted into the protective cap to the first depth of insertion and preventing the syringe to be inserted into the protective cap to the second depth of insertion, wherein removal of the spacer element from the mounted condition on the syringe permits insertion of the syringe into the protective cap to the second depth of insertion to resist removal of the protective cap from the syringe; and
    wherein the spacer element is fully separable from the syringe and the protective cap to permit the spacer element to fall away from the syringe and the protective cap when the protective cap is removed from the syringe such that the spacer element is absent during any reinsertion of the syringe into the protective cap.

2. The system of claim 1 wherein the locking structure comprises a first component on the syringe and a second component on the protective cap, the first and second components being interlockable when the syringe is inserted into the protective cap to the second depth of insertion to resist removal of the protective cap from the syringe.

3. The system of claim 2 wherein the first component comprises at least one first locking tab on the transition portion of the barrel and the second component comprises at least one second locking tab on the interior surface of the protective cap.

4. The system of claim 3 wherein the at least one first locking tab is inclined away from the needle and the at least one second locking tab is inclined toward the distal end of the protective cap.

5. The system of claim 3 wherein the at least one first locking tab comprises a pair of first locking tabs extending in substantially opposite directions from the syringe and the at least one second locking tab comprises a pair of second locking tabs extending substantially toward each other from opposite sides of the interior surface of the protective cap.

6. The system of claim 1 wherein the spacer element comprises a loop extending about the transition portion of the syringe when the spacer element is mounted on the syringe.

7. The system of claim 1 wherein the spacer element is configured to loosely fit on the transition portion of the syringe such that the spacer element is able to fall away from the mounted condition on the syringe when the protective cap is removed from the syringe.

8. The system of claim 1 wherein the protective cap has at least one exterior ridge on the exterior surface of the protective cap.

9. The system of claim 8 wherein the at least one exterior ridge comprises at least a pair of exterior ridges extending in substantially opposite directions for engaging opposite sections of the inner surface of a tubular element.

10. The system of claim 1 wherein the locking structure comprises a first component on the syringe and a second component on the protective cap, the first and second components being interlockable when the syringe is inserted into the protective cap to the second depth of insertion to resist removal of the protective cap from the syringe;
    wherein the first component comprises at least one first locking tab on the transition portion of the barrel and the second component comprises at least one second locking tab on the interior surface of the protective cap;
    wherein the at least one first locking tab is inclined away from the needle and the at least one second locking tab is inclined toward the distal end of the protective cap;
    wherein the at least one first locking tab comprises a pair of first locking tabs extending in substantially opposite directions from the syringe and the at least one second locking tab comprises a pair of second locking tabs extending substantially toward each other from opposite sides of the interior surface of the protective cap;
    wherein the spacer element comprises a loop extending about the transition portion of the syringe when the spacer element is mounted on the syringe;
    wherein the spacer element is configured to loosely fit on the transition portion of the syringe such that the spacer element is able to fall away from the mounted condition on the syringe when the protective cap is removed from the syringe; and
    wherein the protective cap has a pair of exterior ridges on the exterior surface of the protective cap, the pair of exterior ridges extending in substantially opposite directions for engaging opposite sections of the inner surface of a tubular element.

11. A syringe retaining system comprising:
    a medicine vial holder comprising a tubular element with an interior passage defined by an inner surface, and a rod on which at least a portion of the tubular element is mounted such that an end portion of the tubular element is substantially hollow; and
    a syringe retaining apparatus comprising:
        a syringe having a barrel with a main portion and a transition portion with a shoulder therebetween, and a needle extending from the transition portion of the barrel;
        a protective cap removably mounted on the syringe, the protective cap being configured to receive the needle of the syringe and at least a portion of the transition portion of the barrel of the syringe, the protective cap having an open proximal end and a closed distal end, the protective cap having a tip portion at the distal end and a flange adjacent to the proximal end, the protective cap having an interior surface and an exterior surface;

a locking structure configured to permit removal of the protective cap from the syringe when the syringe is inserted to a first depth of insertion into the protective cap and to resist removal of the protective cap from the syringe when the syringe is inserted into the protective cap to a second depth of insertion, the second depth of insertion of the syringe into the protective cap being deeper into the protective cap than the first depth of insertion;

a spacer element removably mounted in a mounted condition on the transition portion of the syringe in a position between the shoulder of the syringe and the flange of the protective cap, the mounted condition of the spacer element being characterized by permitting the syringe to be inserted into the protective cap to the first depth of insertion and preventing the syringe to be inserted into the protective cap to the second depth of insertion, wherein removal of the spacer element from the mounted condition on the syringe permits insertion of the syringe into the protective cap to the second depth of insertion to resist removal of the protective cap from the syringe;

wherein the spacer element is fully separable from the syringe and the protective cap to permit the spacer element to fall away from the syringe and the protective cap when the protective cap is removed from the syringe such that the spacer element is absent during any reinsertion of the syringe into the protective cap; and wherein the protective cap has at least one exterior ridge on the exterior surface of the protective cap configured to engage the inner surface when the tip portion of the protective cap is inserted into the interior passage of the tubular element.

12. The system of claim 11 wherein the at least one exterior ridge comprises at least a pair of exterior ridges extending in substantially opposite directions for engaging opposite sections of the inner surface of the tubular element.

13. The system of claim 11 wherein the locking structure comprises a first component on the syringe and a second component on the protective cap, the first and second components being interlockable when the syringe is inserted into the protective cap to the second depth of insertion to resist removal of the protective cap from the syringe.

14. The system of claim 13 wherein the first component comprises at least one first locking tab on the transition portion of the barrel and the second component comprises at least one second locking tab on the interior surface of the protective cap.

15. The system of claim 11 wherein the spacer element comprises a loop extending about the transition portion of the syringe when the spacer element is mounted on the syringe.

16. The system of claim 11 wherein the spacer element is configured to loosely fit on the transition portion of the syringe such that the spacer element is able to fall away from a mounted condition on the syringe when the protective cap is removed from the syringe.

* * * * *